US008609895B2

(12) United States Patent
Saladino et al.

(10) Patent No.: US 8,609,895 B2
(45) Date of Patent: Dec. 17, 2013

(54) PROCESS FOR THE OXIDATION OF ALCOHOL AND/OR ALDEHYDE GROUPS

(75) Inventors: Raffaele Saladino, Rome (IT); Angela Farina, Rome (IT)

(73) Assignee: Solvay SA, Brussels (BE)

( * ) Notice: Subject to any disclaimer, the term of this patent is extended or adjusted under 35 U.S.C. 154(b) by 526 days.

(21) Appl. No.: 13/054,170

(22) PCT Filed: Jul. 16, 2009

(86) PCT No.: PCT/EP2009/059180
§ 371 (c)(1),
(2), (4) Date: Jan. 14, 2011

(87) PCT Pub. No.: WO2010/007139
PCT Pub. Date: Jan. 21, 2010

(65) Prior Publication Data
US 2011/0124889 A1    May 26, 2011

(30) Foreign Application Priority Data

Jul. 18, 2008   (EP) ..................... 08160771

(51) Int. Cl.
*C07C 51/285*    (2006.01)
*C07D 307/60*    (2006.01)
(52) U.S. Cl.
USPC .......................... 562/533; 549/262
(58) Field of Classification Search
USPC .......................... 562/533; 549/262
See application file for complete search history.

(56) References Cited

U.S. PATENT DOCUMENTS

2006/0070953 A1    4/2006    Villanova et al.

FOREIGN PATENT DOCUMENTS

WO       WO 0061639 A1    10/2000

OTHER PUBLICATIONS

Herrmann, Wolfgang A., et al—"Darstellung and Kristallstruktur von (Penicillaminato-O,S,N)bismut(III)-chlorid"—Chem. Ber. 1993, 126, 895-898; 4 pgs.
Al-Ajlouni, Ahmad M., et al—"Epoxidation of Styrenes by Hydrogen Peroxide As Catalyzed by Methylrhenium Trioxide"—J. Am Chem Soc 1995, 117, 9243-9250; 8 pgs.
Saladino, Raffaele, et al—"A new and efficient synthesis of *ortho*- and, *para*-benzoquinones of cardanol derivatives by the catalytic system MeReO3-H2O2"—J. Chem Soc. Perkin Trans 1, 2000, 581-586; 6 pgs.
Saladino, Raffaele, et al—"Preparation and Structural Characterization of Polymer-Supported Methylrhenium Trioxide Systems as Efficient and Selective Catalysts for the Epoxidation of Olefins"—J. Org Chem 2002, 67, 1323-1332; 10 pgs.
Ullmann's Encyclopedia of Industrial Chemistry—DOI 10,100214356007.a05_079 "Carbohydrates" 2003; Wiley VCH Verlag GmbH & Co., KGaA, Weinheim; 43 pgs.
Ullmann's Encyclopedia of Industrial Chemistry—DOI 10,100214356007.a12_119.pub2 "Furfural and Derivatives" 2007; Wiley VCH Verlag GmbH & Co., KGaA, Weinheim; 29 pgs.
Ullmann's Encyclipedia of Industrial Chemistry—DOI 10.1002/14356007.a16_053 "Maleic and Fumaric acids" 2000; Wiley VCH Verlag GmbH & Co., KGaA, Weinheim; 14 pgs.
Saladino, Raffaele, et al—"Selective oxidation of phenol and anisole derivatives to quinones with hydrogen peroxide and polymer-supported methylrhenium trioxide systems"—Tetrahedron 58, 2002, 8493-8500; 8 pgs.
Crestini, Claudia, et al—"Immobilized methyltrioxo rhenium (MTO)/H2O2 systems for the oxidation of lignin and lignin model compounds"—Bioorganic & Medicinal Chemistry 14, 2006, 5292-5302; 11 pgs.
Herrmann, Wolfgang A., et al—"The selective catalytic oxidation of terminal alcohols : a novel four-component system with MTO as catalyst"—Journal of Organometallic Chemistry—579, 1999, 404-407; 4 pgs.
Adam, Waldemar, et al—Catalytic Oxidation of Phenols to p-Quinones with the Hydrogen Peroxide and Methyltrioxorhenium (VII) System—J. Org. Chem. 1994, 59, 8281-8283; 3 pgs.
Yamazaki, Shigekazu—"Oxidation of Benzaldehydes Catalyzed by Methyltrioxorhenium with Hydrogen Peroxide"—Chemistry Letters 1995; 2, 127-128; 3 pgs.
Rudler, Henri, et al—"MTO catalyzed oxidation of aldehyde N,N-dimethylhydrazones with hydrogen peroxide : high yield formation of nitriles and N-methylene-N-methyl-N-oxide"—Chem Commun. 1998, 19, 2145-2146; 2 pgs.
Zauche, Timothy H., et al—"Oxidation of Alcohols by Hydrogen Peroxide, Catalyzed by Methyltrioxorhenium (MTO) : A Hydride Abstraction"—Inorg Chem 1998, 37, 6827-6831; 5 pgs.
Espenson, James H., et al—Bromide Ions and Methyltrioxorhenium Cocatalysts for Hydrogen Peroxide Oxidations and Brominations—J. Org Chem. 1999, 64, 1191-1196; 6 pgs.
Boyd, Ewan C., et al—""Green" oxidation reactions—application to carbohydrate chemistry"—Green Chemistry 2003, 5, 679-681; 3 pgs.
Berninni, Roberta, et al—"Oxidation of aromatic aldehydes and ketones by H2O2/CH3ReO3 in ionic liquids : a catalytic efficient reaction to achieve dihydric phenols"—Tetrahedron 61, 2005, 1821-1825; 5 pgs.
Jain, Suman L., et al—"Methyltrioxorhenium and Sodium Bromide-Catalyzed Oxidation of Alcohols to Carbonyl Compounds with H2O2 Using 1-Butylmethylimidazolium Tetrafluoroborate Ionic Liquid as Novel Recyclable Green Solvent"—Bull Chem Soc Japan 79 (10), 1601-1603 (2006); 4 pgs.
Rost, Alexandra M.J., et al—"Behaviour of dimeric methylrhenium (VI) oxides in the presence of hydrogen peroxide and its consequences for oxidation catalysis"—New J Chem 2006, 30, 1599-1605; 7 pgs.
Herrmann, W.A., et al—"Green catalysis for ecologically responsible oxidation of organic substrates and renewable resources"—Book of Abstracts 218th ACS National Meeting New Orleans Aug. 22-26, 1999; 1 pg.

*Primary Examiner* — Bernard Dentz
(74) *Attorney, Agent, or Firm* — Beatrice C. Ortego

(57) ABSTRACT

A process for the oxidation of alcohol and/or aldehyde groups with a peroxo compound in the presence of a heterogeneous rhenium based catalyst, and a co-catalyst. The process of the invention may, for example, be applied to the manufacture of maleic acid which can be dehydrated to lead to maleic anhydride.

16 Claims, No Drawings

PROCESS FOR THE OXIDATION OF ALCOHOL AND/OR ALDEHYDE GROUPS

CROSS-REFERENCE TO RELATED APPLICATIONS

The present application is a U.S. national stage application under 35 U.S.C. §371 of International Application No. PCT/EP2009/059180 filed Jul. 16, 2009, which claims the benefit of the European application no. 08160771.5 filed on Jul. 18, 2008, the whole content of this application being herein incorporated by reference for all purposes.

The present application claims the benefit of the European application no. 08160771.5 filed on Jul. 18, 2009, herein incorporated by reference.

The present invention relates to a process for the oxidation of alcohol and/or aldehyde groups. In particular, it relates to an oxidizing process based on peroxo compounds, heterogeneous rhenium based catalysts and co-catalysts.

The use of rhenium based catalysts to activate hydrogen peroxide for the oxidation of various functional groups, and especially alcohol and/or aldehyde groups, is known in the prior art. The catalytic cycle of methyltrioxorhenium is for example disclosed in W. A. Hermann et al., Chemische Berichte, 126, 4 (1993) and in J. H. Espenson et al., J. Am. Chem. Soc., 117, 9243 (1995).

Applications of rhenium based catalysts are disclosed, for example, in the international patent application WO 00/61639 which relates to oxidized starch obtained by oxidizing native starch in an acidic solvent in the presence of hydrogen peroxide, rhenium (VI) or (VII) oxide, methyltrioxorhenium (MTO) or alkyl rhenium oxide in homogeneous phase, a ditertiary alkyl nitroxyl and hydrogen halide.

Another use is disclosed in the US patent application 2006/0070953 A1 which relates to the catalytic oxidation of tyrosol into hydroxytyrosol in the presence of hydrogen peroxide, a protic solvent, and methyltrioxorhenium (MTO), preferably in homogeneous phase.

A third example is the use of hydrogen peroxide and of methyltrioxorhenium (MTO) in homogeneous phase for the synthesis of ortho- and para-benzoquinones of cardanol derivatives, disclosed in an article from R. Saladino et al., *J. Chem. Soc., Perkin Trans.* 1, 581-586 (2000) which is incorporated by reference. The oxidation reaction of various benzoquinones of cardanol derivatives was tested in various solvents selected from acetic acid, ethanol, and a mixture ethanol—tetrafluoroboric acid ($HBF_4$) in excess. Depending on the derivatives tested, the best results were obtained using acetic acid or the mixture ethanol—$HBF_4$.

These processes have the disadvantage to be conducted in homogeneous phase, which do not allow an easy recovery of the catalyst.

It is also known to proceed to the oxidation of olefins into epoxides in heterogeneous phase, using polymer-supported rhenium based catalysts. Such polymer-supported catalysts are disclosed, for example, in an article from R. Saladino et al., *J. Org. Chem.*, 67, 1323-1332 (2002). The heterogeneization of rhenium based catalysts by using a polymeric support allows an easier recovery of the catalyst and, sometimes, may improve the reactivity.

Nevertheless, there is still a need for improved processes for the oxidation of alcohol and/or aldehyde groups, leading to high yields, an easy recovery of the catalyst, and a good stability and reuse of the catalyst.

The purpose of the present invention is to provide a new process for the oxidation of alcohol and/or aldehyde groups having improved properties compared to the processes of the prior art.

The present invention therefore relates to a process for the oxidation of alcohol and/or aldehyde groups comprising the treatment of said alcohol and/or aldehyde groups with at least one oxidizing agent chosen from peroxo compounds in the presence of at least one solvent, of at least one heterogeneous rhenium based catalyst, and of a co-catalyst selected from the group consisting of $HBF_4$ and salts thereof.

According to the present invention, it has been surprisingly found that, when alcohol and/or aldehyde groups are oxidized with a peroxo compound in the presence of a heterogeneous rhenium based catalyst and a co-catalyst such as $HBF_4$ or a salt thereof, the stability and reuse of the catalyst is improved. Furthermore, according to the process of the invention, it is easier to recover the catalyst from the reaction mixture compared to reactions conducted in homogeneous phase, the selectivity of the reaction can be modified, and the amount of active rhenium compound added to the reaction mixture can be drastically reduced. This process is thus especially advantageous compared to the processes of the prior art.

By alcohol and aldehyde groups, it is intended primary and secondary alcohol and aldehyde groups. According to the present invention, such groups may be present on any substrates. For example, the compounds may be linear, branched or cyclic alkyl alcohols or aldehydes, aromatic alcohols or aldehydes such as benzaldehyde and benzyl alcohol derivatives, as well as high and low molecular weight carbohydrates and carbohydrate derivatives. In a preferred embodiment, the oxidation process of the present invention is applied to at least one compound selected from the group consisting of linear, branched or cyclic alkyl alcohols and linear, branched or cyclic alkyl aldehydes, especially to carbohydrates and carbohydrate derivatives, for example to high and low molecular weight carbohydrates and carbohydrate derivatives, advantageously to low molecular weight carbohydrates and low molecular weight carbohydrate derivatives. High molecular weight carbohydrates, also called polysaccharides, are composed of monosaccharide units, usually in an amount of more than 10 to 10000 units, preferably from 25 to 5000 units, for example from 50 to 500 units, a few of them being made up of considerably more units. High molecular weight carbohydrates include, for example, starch, cellulose, hemicellulose and chitin. Cellulose has an average molecular mass equivalent to about 5000 units. Low molecular weight carbohydrates include mono and oligosaccharides, composed of 1 to 10 monosaccharide residues, preferably mono- and disaccharides. The term "monosaccharide" denotes a single sugar unit without glycosidic connection to other such units. Chemically, monosaccharides are either polyhydroxyaldehydes or aldoses, such as glucose, or polyhydroxyketones or ketoses, such as fructose. Depending on their number of carbon atoms, monosaccharides are classified in hexoses (6C) and pentoses (5C). Monosaccharides with fewer (trioses, tetroses) or more carbon atoms (heptoses, octoses) are rare. Preferred low molecular weight carbohydrates according to the present invention are monosaccharides, especially pentoses and hexoses. Carbohydrate derivatives may be glycosides, alditols, furan derivatives, such as furfural and 5-hydroxymethylfurfural (HMF), etc. Some general information about carbohydrates and carbohydrate derivatives may for example be found in online Ullmann's Encyclopedia of Industrial Chemistry, DOI 10.100214356007.a05_079, "Carbohydrates" (2003), incorporated herewith by reference.

One of the essential features of the present invention resides in the nature of the heterogeneous catalyst. The term "homogeneous catalyst" means that the catalyst and reactants or their solution form a common physical phase, then the reaction is called homogeneously catalyzed. The term "heterogeneous catalyst" is used when the system is such that catalyst and reactants form separate physical states. The heterogeneous catalysts may be unsupported (bulk) catalysts insoluble in the reactant mixture, or supported catalysts.

The heterogeneous catalyst of the invention may be chosen from insoluble unsupported rhenium based catalysts and supported rhenium based catalysts, preferably from supported rhenium based catalysts. Supported rhenium based catalysts usually comprise an inert polymeric matrix (support) and a rhenium compound (active part of the catalyst).

The rhenium compound according to the process of the invention is usually selected from rhenium (VI) oxide ($ReO_3$), rhenium (VII) oxide ($R_2O_7$), methyl rhenium trioxide ($CH_3ReO_3$), a $C_2$ to $C_{20}$ alkyl rhenium oxide, a $C_3$ to $C_{10}$ cycloalkyl rhenium oxide. The rhenium compound of the invention is preferably methyltrioxorhenium (MTO).

The inert polymeric matrix of the catalyst according to the invention may be selected from poly(4-vinylpyridine) (PVP), poly(4-vinylpyridine N-oxide) (PVPN), polystyrene (PS) and mixtures thereof. Such catalyst supports are disclosed, for example, in an article by R. Saladino et al, J. Org. Chem. 67, 1323-1332 (2002), incorporated herewith by reference. It has to be noted that the supports may differ by their crosslinking with divinylbenzene. The crosslinking of PVP, PVPN or PS with divinylbenzene is usually of from 1 to 50%, preferably of from 2 to 25%.

In the process of the invention, the amount of rhenium compound by weight of the support, expressed as the loading factor (mmol/g), is usually at least 0.1, in particular at least 0.3, especially at least 0.5, values of at least 1 giving good results. The amount of rhenium compound by weight of the support, expressed as the loading factor (mmol/g), is in general of at most 10, in many cases at most 5, preferably at most 3. Suitable ranges for the loading factor of the catalyst are from 0.1 to 10, preferably from 0.5 to 5, more preferably from 1 to 3.

Another essential feature of the present invention is the presence of a peroxo compound which may be selected from hydrogen peroxide or hydrogen peroxide sources such as alkali or alkaline earth metal percarbonates, for example sodium percarbonate; alkali or alkaline earth metal perborates, such as sodium perborate; alkaline earth metal or metal peroxides, such as calcium peroxide, magnesium peroxide, zinc peroxide and mixed calcium/magnesium peroxide; and their mixtures. The peroxo compound is preferably an aqueous hydrogen peroxide solution. Such aqueous hydrogen peroxide solution usually has a concentration of from 5 to 70 weight %, preferably of from 20 to 50 weight %, in general about 35 weight %.

A third essential feature of the present invention resides in the presence of at least one solvent. In the invention, the solvent may be selected from water; carboxylic acids such as acetic acid; organic solvents such as methanol, ethanol, propanol, acetonitrile, dichloromethane; ionic liquids such as 1-butyl-3-methylimidazolium tetrafluoroborate ([BMIM] [$BF_4$]); and mixtures thereof. According to the present invention, the solvent is preferably selected from protic solvents such as water; acetic acid; $C_1$ to $C_3$ alcohols, especially methanol or ethanol; and mixtures thereof.

In the process of the invention, the amount of heterogeneous rhenium based catalyst is generally of at least 0.1% by weight of the compound to be oxidized, preferably at least 0.5%, more preferably at least 1%, in particular at least 2%. The amount of heterogeneous rhenium based catalyst used in the process of the invention is in general of at most 15% by weight of the compound to be oxidized, especially at most 12%, particularly at most 10%, especially at most 7%. In most cases, the amount of heterogeneous rhenium based catalyst by weight of the compound to be oxidized is of from 0.1 to 10%, ranges of from 1 to 7% giving good results, for example around 5%.

A fourth essential feature of the present invention is the presence of a co-catalyst. Said co-catalyst may be selected from $HBF_4$, salts thereof and mixtures thereof. According to the process of the invention, the salt of $HBF_4$ is preferably selected from the group consisting of the sodium salt, ammonium salt, lithium salt and mixtures thereof. The co-catalyst is usually present in an amount of at least 0.1% by volume of the solvent, preferably at least 0.5% and of at most 10%, especially at most 5%. An amount of about 1% of co-catalyst by weight of compound to be oxidized is for example suitable. In the process of the present invention, said co-catalyst is preferably $HBF_4$.

The amount of peroxo compound used in the present invention is usually of at least 1 equivalent of the optionally substituted furfural, in particular at least 2 equivalents, values of at least 4 equivalents and more specifically at least 5 equivalents giving good results. The amount of peroxo compound is in general of at most 20 equivalents of the optionally substituted furfural, in many cases at most 15 equivalents, values of at most 10 equivalents being common.

The oxidation process according to the present invention is usually carried out at a temperature of at least 5° C., preferably at least 10° C., more preferably at least 15° C. The process of the invention is in general carried out at a temperature of at most 100° C., particularly at most 75° C., especially at most 50° C., with particular preference at most 30° C. The process is advantageously carried out at a temperature from 5 to 50° C., preferably from 10 to 45° C., especially from 15 to 30° C., advantageously around room temperature, for example around 20° C.

The process of the invention may be carried out at subatmospheric pressures, atmospheric pressure, or elevated pressure, preferably at atmospheric pressure.

The process of the invention is usually carried out during from 1 to 100 hours, preferably from 12 to 72 hours, more preferably from 24 to 48 hours.

The oxidation process of the invention may be carried out in any suitable reactor. An example of a suitable reactor is a plug-flow reactor equipped with a catalytic bed. Another example is any suitable reactor wherein the catalyst is maintained in suspension.

The process of this invention may be carried out in a batch, continuous, or semi-continuous manner, preferably as a continuous process.

In a preferred embodiment, the process of the invention may be applied to carbohydrates, especially to low molecular weight carbohydrates and derivatives thereof. The invention may for example be applied to low molecular weight carbohydrate derivatives such as furfural, 5-hydroxymethyl furfural and mixtures thereof.

Furfural, or 2-furancarbonal or 2-furaldehyde, is a well known chemical product produced by acid-catalyzed hydrolysis of hemicellulose, especially from hemicellulose-rich agricultural wastes, the resulting monosaccharides being then dehydrated to furfural. 5-hydroxymethyl furfural (HMF) is produced according to a similar process applied to cellulose or starch. The hexoses resulting from the acid-catalyzed hydrolysis of cellulose or starch can be readily transformed into HMF by acid-induced elimination of three moles of water. General information on these compounds is found in online Ullmann's Encyclopedia of Industrial Chemistry, DOI 10.1002/14356007.a12_119.pub2, "Furfural and Derivatives" (2007).

If the process of the invention is applied to furfural and/or to 5-hydroxymethyl furfural (HMF), it is possible to prepare various monocarboxylic acids such as glycolic acid, furoic acid, and 5-hydroxy methyl furoic acid, as well as various dicarboxylic acids such as maleic acid, succinic acid, fumaric acid, and malic acid. In a particularly preferred embodiment, the process of the present invention is used for the preparation of maleic acid with high yields.

The present invention thus also relates to a process for the preparation of maleic acid as well as to a process for the preparation of maleic anhydride, comprising the preparation of maleic acid according to the process of the present invention applied to carbohydrate derivatives selected from furfural, 5-hydroxymethyl furfural and mixtures thereof, and a further dehydration step. Such dehydration step can be performed according to any method known in the prior art. For general information, see for example online Ullmann's Encyclopedia of Industrial Chemistry, DOI 10.1002/14356007.a16_053, "Maleic and Fumaric Acids" (2000). The maleic acid dehydration can for example be performed by heating maleic acid up to 160° C. while eliminating the water. This reaction is quantitative.

If maleic acid is not very important economically, maleic anhydride is a commodity chemical having considerable industrial importance. Indeed, maleic anhydride can be used for both polycondensation and polyaddition. Polyester and alkyd resins, lacquers, plasticizers, copolymers, and lubricants are the most important technical end products. Polyester and alkyd resins are especially used in the production of fiberglass reinforced plastics, in the construction and electrical industries, and in pipeline and marine construction. Smaller amounts of maleic anhydride are used in the production of pesticides and growth inhibitors, or of surfactants. More information about maleic acid and maleic anhydride is found, for example, in online Ullmann's Encyclopedia of Industrial Chemistry, DOI 10.1002/14356007.a16_053, "Maleic and Fumaric Acids" (2000).

The industrial preparation process of maleic anhydride is usually based on the catalytic oxidation of suitable hydrocarbons in the gas phase, especially benzene and, more recently, $C_4$ hydrocarbons. Maleic anhydride can also be obtained by dehydration from maleic acid but this is not the preferred industrial manufacturing process.

Thus, a particular advantage of the present invention applied to the oxidation of furfural and/or 5-hydroxymethyl furfural is the possibility to prepare specialty and commodity chemicals starting from a renewable feedstock as furfural and 5-hydroxymethyl furfural (HMF) are biomass based products, produced from carbohydrate sources and especially from hemicellulose and cellulose wastes such as agricultural and forestry wastes, which are interesting alternative to petrochemical products. This advantage is particularly important in the framework of the responsible care and the sustainable development.

The present invention is further illustrated below without limiting the scope thereto.

COMPARATIVE EXAMPLES 1 TO 3

Oxidation of 5-Hydroxymethyl Furfural in Homogeneous Conditions 5-hydroxymethyl furfural (HMF) was oxidized with 10 equivalents of hydrogen peroxide (35% by weight in aqueous solution) in the presence of methyltrioxorhenium in an amount of 5% by weight of HMF, at a temperature about 20° C. during 24 to 48 hours, until the conversion of HMF was complete, in various solvents.

The results of the reactions are summarized in Table 1 below.

TABLE 1

|  |  | Example n° (solvent) | | |
|---|---|---|---|---|
|  |  | Comp. Ex. 1 (acetic acid) | Comp. Ex. 2 (ethanol) | Comp. Ex. 3 (dichloromethane/ acetonitrile 1:1 v/v) |
| Resulting products (%) | Glycolic acid | 55 | 23 | 19 |
|  | Maleic acid | 14 | 29 | 20 |
|  | Succinic acid | 1 | 16 | 35 |
|  | Fumaric acid | 1 | 0 | 8 |
|  | Malic acid | 29 | 11 | 0 |
|  | 5-hydroxymethyl-2-furoic acid | 0 | 6 | 10 |

COMPARATIVE EXAMPLES 4 TO 9

Oxidation of Furfural in Homogeneous Conditions

Furfural was oxidized with 9 equivalents of hydrogen peroxide (35% by weight in aqueous solution) in the presence of methyltrioxorhenium in an amount of 5% by weight of furfural, at a temperature about 20° C. during 24 to 48 hours, until the conversion of furfural was complete in various solvents and in the optional presence of $HBF_4$ as co-catalyst.

The results of the reactions are summarized in Table 2 below.

TABLE 2

|  |  | Example n° (solvent + optional co-catalyst) | | | | | |
|---|---|---|---|---|---|---|---|
|  |  | Comp. Ex. 4 ($H_2O$) | Comp. Ex. 5 (acetic acid) | Comp. Ex. 6 (ethanol) | Comp. Ex. 7 (ethanol + 1% v/v $HBF_4$) | Comp. Ex. 8 ($CH_2Cl_2/CH_3CN$ 1:1 v/v) | Comp. Ex. 9 ([BMIM][$BF_4$]) |
| Resulting products (%) | Maleic acid | 44 | 81 | 49 | 60 | 66 | 66 |
|  | Succinic acid | 26 | 0.5 | 8 | 1 | 3 | 12 |

TABLE 2-continued

| | | Comp. Ex. 4 (H₂O) | Comp. Ex. 5 (acetic acid) | Comp. Ex. 6 (ethanol) | Comp. Ex. 7 (ethanol + 1% v/v HBF₄) | Comp. Ex. 8 (CH₂Cl₂/CH₃CN 1:1 v/v) | Comp. Ex. 9 ([BMIM][BF₄]) |
|---|---|---|---|---|---|---|---|
| | Malic acid | 6 | 5 | 6 | 4 | 8 | 0 |
| | Fumaric acid | 2 | 5 | 2 | 3 | 4 | 13 |
| | 2-furoic acid | 12 | 4 | 20 | 13 | 10 | 7 |

COMPARATIVE EXAMPLES 10 TO 12 AND EXAMPLES 13 TO 14

Oxidation of Furfural in Heterogeneous Conditions (Catalyst Supported on Poly(4-Vinylpyridine))

Furfural was oxidized with 5 equivalents of hydrogen peroxide (35% by weight in aqueous solution) in the presence of 5% by weight of methyltrioxorhenium supported onto poly (4-vinylpyridine) with a loading factor of 2 mmol/g, at a temperature about 20° C. during 24 hours, in various solvents and in the optional presence of HBF₄ as co-catalyst.

The results of the reactions are summarized in Table 3 below.

TABLE 3

| | | Comp. Ex. 10 (H₂O) | Comp. Ex. 11 (acetic acid) | Comp. Ex. 12 (H₂O + acetic acid (50:50 v/v) | Ex. 13 (H₂O + 1% v/v HBF₄) | Ex. 14 (EtOH + 1% v/v HBF₄) |
|---|---|---|---|---|---|---|
| Resulting products (%) | Maleic acid | 5 | 51 | 40 | 52 | 62 |
| | Succinic acid | 5 | 0 | 6 | 5 | 0 |
| | Malic acid | 0 | 5 | 0 | 0 | 0 |
| | Fumaric acid | 3 | 4 | 3 | 3 | 3 |
| | 2-furoic acid | 72 | 7 | 41 | 33 | 19 |

COMPARATIVE EXAMPLE 15 AND EXAMPLE 16

Stability and Reuse of the Catalyst of Examples 11 and 14

Examples 11 and 14 were reproduced respectively 4 and 3 times, reusing the same catalyst.

The results are summarized in Table 4 below.

TABLE 4

| | Comp. Ex. 15 (acetic acid) Yields (%) | | Ex. 16 (EtOH + 1% v/v HBF₄) Yields (%) | |
|---|---|---|---|---|
| | Maleic acid | 2-furoic acid | Maleic acid | 2-furoic acid |
| Run 1 | 51 | 7 | 60 | 30 |
| Run 2 | 10 | 42 | 58 | 40 |
| Run 3 | 20 | 33 | 32 | 44 |
| Run 4 | 26 | 11 | Not measured | Not measured |

COMPARATIVE EXAMPLES 17 AND 19 AND EXAMPLE 18

Oxidation of Furfural in Heterogeneous Conditions (Catalyst Supported on Polystyrene)

Furfural was oxidized with 9 equivalents of hydrogen peroxide (35% by weight in aqueous solution) in the presence of 5% by weight of methyltrioxorhenium supported onto polystyrene with a loading factor of 2 mmol/g, at a temperature about 20° C. during 48 to 72 hours, until the conversion of furfural was complete, in various solvents and in the optional presence of HBF₄ as co-catalyst.

The results of the reactions are summarized in Table 5 below.

TABLE 5

| | | Example n° (solvent + optional co-catalyst | | |
|---|---|---|---|---|
| | | Comp. Ex. 17 (acetic acid) | Ex. 18 (EtOH + 1% v/v HBF$_4$) | Comp. Ex. 19 (CH$_2$Cl$_2$/CH$_3$CN 1:1) |
| Resulting products (%) | Maleic acid | 84 | 84 | 44 |
| | Succinic acid | 3 | 5 | 10 |
| | Malic acid | 9 | 0 | 11 |
| | Fumaric acid | 1 | 0 | 2 |
| | 2-furoic acid | 0 | 8 | 10 |
| | (furanone) | 0 | 0 | 5 |

COMPARATIVE EXAMPLES 20 TO 21

Stability and Reuse of the Catalyst of Examples 17 and 19

Examples 17 and 19 were reproduced 5 times, reusing the same catalyst. The only difference is that runs 3, 4 and 5 of example 21 were conducted at 40° C. rather than 20° C.

The results are summarized in Table 6 below.

TABLE 6

| | Comp. Ex. 20 (acetic acid) Yields (%) | | Comp. Ex. 21 (CH$_2$Cl$_2$/CH$_3$CN 1:1) Yields (%) | |
|---|---|---|---|---|
| | Maleic acid | Malic acid | Maleic acid | Malic acid |
| Run 1 | 84 | 8 | 44 | 11 |
| Run 2 | 31 | 20 | 54 | 9 |
| Run 3 | 44 | 23 | 29 | 17 |
| Run 4 | 40 | 20 | 35 | 8 |
| Run 5 | 32 | 15 | 42 | 19 |

COMPARATIVE EXAMPLES 22 TO 24 AND EXAMPLE 25

Oxidation of Furfural in Heterogeneous Conditions (Catalyst Supported on Polystyrene)

Furfural was oxidized with 5 equivalents of hydrogen peroxide (35% by weight in aqueous solution) in the presence of 5% by weight of methyltrioxorhenium supported onto polystyrene, at a temperature about 20° C. during 24 hours, in various solvents and in the optional presence of HBF$_4$ as co-catalyst.

The results of the reactions are summarized in Table 7 below.

TABLE 7

| | | Example n° (solvent + optional co-catalyst | | | |
|---|---|---|---|---|---|
| | | Comp. Ex. 22 (No catalyst) | Comp. Ex. 23 (H$_2$O) | Comp. Ex. 24 (H$_2$O + acetic acid 50:50 v/v) | Ex. 25 (H$_2$O + 1% v/v HBF$_4$) |
| Resulting products (%) | Maleic acid | 2 | 82 | 76 | 71 |
| | Succinic acid | 0 | 0 | 6 | 17 |
| | 2-furoic acid | 4 | 18 | 3 | 4 |

COMPARATIVE EXAMPLES 26 TO 27 AND EXAMPLE 28

Stability and Reuse of the Catalyst of Examples 23, 24 and 25

Examples 23, 24 and 25 were reproduced respectively 4, 3 and 7 times, reusing the same catalyst.

The results are summarized in Table 8 below.

TABLE 8

| | Comp. Ex. 26 (H$_2$O) Yields (%) | | Comp. Ex. 27 (H$_2$O + acetic acid) Yields (%) | | Ex. 28 (H$_2$O + 1% v/v HBF$_4$) Yields (%) | | |
|---|---|---|---|---|---|---|---|
| | Maleic acid | 2-furoic acid | Maleic acid | 2-furoic acid | Maleic acid | Succinic acid | 2-furoic acid |
| Run 1 | 82 | 18 | 76 | 3 | 71 | 17 | 4 |
| Run 2 | 8 | 63 | 36 | 49 | 90 | 10 | 0 |
| Run 3 | 6 | 63 | 2 | 80 | 89 | 6 | 5 |
| Run 4 | 1 | 87 | Not measured | Not measured | 81 | 10 | 9 |
| Run 5 | Not measured | Not measured | Not measured | Not measured | 82 | 10 | 7 |
| Run 6 | Not measured | Not measured | Not measured | Not measured | 66 | 27 | 3 |
| Run 7 | Not measured | Not measured | Not measured | Not measured | 77 | 12 | 10 |

These examples show that it is possible to prepare various specialty and commodity chemicals, especially maleic acid, according to the process of the present invention. These examples also show that it is possible, using an heterogeneous supported rhenium based catalyst and a co-catalyst according to the invention, to improve the stability and reuse of the catalyst.

Furthermore, depending on the reaction conditions, a yield conversion of up to 85% by weight of maleic acid can be obtained. This maleic acid can then be subsequently dehydrated to yield maleic anhydride with a quantitative yield, by a thermal treatment around 160° C. while eliminating the water. The overall yield to produce maleic anhydride from furfural and/or 5-hydroxymethyl furfural can thus be higher than 80%, depending on the reaction conditions. This yield is higher than the yield usually reached when maleic anhydride is prepared according to usual manufacturing processes, from benzene or butane (respectively about 70 and 60% yield).

The invention claimed is:

1. A process for the oxidation of at least one of an alcohol and an aldehyde group comprising the treatment of said group with at least one oxidizing agent chosen from peroxo compounds in the presence of at least one solvent, of at least one heterogeneous rhenium based catalyst, and of a co-catalyst selected from the group consisting of $HBF_4$ and salts thereof.

2. The process according to claim 1, wherein the peroxo compound is selected from hydrogen peroxide or hydrogen peroxide sources selected from the group consisting of alkali or alkaline earth metal percarbonates, alkali or alkaline earth metal perborates, and alkaline earth metal or metal peroxides.

3. The process according to claim 1, wherein the heterogeneous rhenium based catalyst is a supported rhenium based catalyst comprising an inert polymeric matrix and a rhenium compound.

4. The process according to claim 3, wherein the inert polymeric matrix is selected from the group consisting of poly(4-vinylpyridine), poly(4-vinylpyridine N-oxide), and polystyrene.

5. The process according to claim 3, wherein the rhenium compound is selected from the group consisting of rhenium (VI) oxide, rhenium (VII) oxide, methyltrioxorhenium, a $C_2$ to $C_{20}$ alkyl rhenium oxide, and a $C_3$ to $C_{10}$ cycloalkyl rhenium oxide.

6. The process according to claim 1, wherein the solvent is selected from the group consisting of water, carboxylic acids, organic solvents, ionic liquids, and mixtures thereof.

7. The process according to claim 1, wherein the salt of $HBF_4$ is selected from the group consisting of the sodium salt, ammonium salt, lithium salt, and mixtures thereof.

8. The process according to claim 1, wherein the oxidation is conducted at a temperature of from 5 to 50° C., during from 12 to 72 hours.

9. The process according to claim 1, wherein the heterogeneous rhenium based catalyst is used in an amount of from 0.1 to 10% by weight of the compound to be oxidized.

10. The process according to claim 3, wherein the supported rhenium based catalyst has a loading factor, defined as mmol of rhenium compound per g of support, of from 0.1 to 10.

11. The process according to claim 1, wherein the oxidizing agent is used in an amount of from 1 to 20 equivalents of the compound to be oxidized.

12. The process according to claim 1 being applied to at least one compound selected from the group consisting of linear, branched or cyclic alkyl alcohols and linear, branched or cyclic alkyl aldehydes.

13. The process according to claim 1, being applied to low molecular weight carbohydrate derivatives from the group consisting of furfural, 5-hydroxymethyl furfural, and mixtures thereof.

14. The process according to claim 13, being suitable for the preparation of maleic acid.

15. The process according to claim 14, comprising a further dehydration step of the maleic acid into maleic anhydride.

16. The process according to claim 1 being applied to at least one compound selected from the group consisting of carbohydrates and carbohydrate derivatives.

* * * * *